(12) United States Patent
Shinohara et al.

(10) Patent No.: US 7,718,847 B2
(45) Date of Patent: May 18, 2010

(54) METHOD OF GENE INTRODUCTION IN IN-VIVO SPERMATOGENIC CELL

(75) Inventors: Takashi Shinohara, Kyoto (JP); Mito Shinohara, Kyoto (JP)

(73) Assignee: Kyoto University, Kyoto-shi (JP)

( * ) Notice: Subject to any disclaimer, the term of this patent is extended or adjusted under 35 U.S.C. 154(b) by 57 days.

(21) Appl. No.: 11/569,646

(22) PCT Filed: May 25, 2005

(86) PCT No.: PCT/JP2005/010002

§ 371 (c)(1),
(2), (4) Date: Aug. 13, 2007

(87) PCT Pub. No.: WO2005/115133

PCT Pub. Date: Dec. 8, 2005

(65) Prior Publication Data

US 2008/0060091 A1 Mar. 6, 2008

(30) Foreign Application Priority Data

May 27, 2004 (JP) .............................. 2004-158174

(51) Int. Cl.
*C12N 15/00* (2006.01)
(52) U.S. Cl. .............................. 800/21; 800/22; 800/23
(58) Field of Classification Search ................... 800/21, 800/22, 23
See application file for complete search history.

(56) References Cited

U.S. PATENT DOCUMENTS

| | | | |
|---|---|---|---|
| 6,316,692 B1 | 11/2001 | Readhead et al. | |
| 7,527,966 B2 * | 5/2009 | Cooper et al. | 435/320.1 |
| 2002/0016977 A1 | 2/2002 | Nakatsuji et al. | |
| 2002/0028488 A1 * | 3/2002 | Singh et al. | 435/70.21 |

FOREIGN PATENT DOCUMENTS

JP 2001-309736 A 11/2001
JP 2003-180197 A 7/2003

OTHER PUBLICATIONS

Byers et al. Am J Anatomy 191:35-47, 1991.*
Yang et al. J Korean Med Sci 21:445-451, 2006.*
Parreira et al. Biol Reprod 67:1232-1241, 2002.*
Hrabia et al. Biol of Reprod 69:1651-1657, 2003.*
Hamra et al., *PNAS*, 99(23): 14931-14936 (Nov. 12, 2002).
Huang et al., *FEBS Letters*, 487: 248-251 (2000).
Ikawa et al., *PNAS*, 99(11): 7524-7529 (May 28, 2002).
Kanatsu-Shinohara et al., *PNAS*, 99(3): 1383-1388 (Feb. 5, 2002).
Kim et al., *Molecular Reproduction and Developments*, 46: 515-526 (1997).
Muramatsu et al., *Biochemical and Biophysical Research Communications*, 233: 45-49 (1997).
Nagano et al., *FEBS Letters*, 475: 7-10 (2000).
Nagano et al., *PNAS*, 98(23): 13090-13095 (Nov. 6, 2001).
Yamazaki et al, *Biology of Reproduction*, 59: 1439-1444 (1998).
Yomogida et al., *Biology of Reproduction*, 67: 712-717 (2002).
Igdoura et al., *Journal of Andrology*, 15(3): 234-243 (1994).
Pogach et al., *Toxicology and Applied Pharmacology*, 98: 350-361 (1989).
Wiebe et al., *Journal of Andrology*, 21(5): 625-635 (2000).

* cited by examiner

*Primary Examiner*—Thaian N Ton
*Assistant Examiner*—Marcia S Noble
(74) *Attorney, Agent, or Firm*—Leydig, Voit & Mayer, Ltd.

(57) ABSTRACT

The present invention provides a method of producing a non-human vertebrate that harbours germ cells having a desired gene transferred thereto, comprising injecting the desired gene to the testis of a non-human vertebrate wherein no tight junction exists between Sertoli cells to transfer the desired gene to germ cells, so as to obtain a non-human vertebrate that harbours the germ cells having the desired gene transferred thereto. Using the method of the present invention, even in animal species and lines for which in vitro transduction has been difficult to date, it is possible to obtain an individual harbouring germ cells, particularly spermatogonial stem cells, having a desired gene transferred thereto, at extremely high efficiency. Also, the fertility of the male to receive an injection of the gene is retained, compared to in vitro transduction of germ cells, because gene transfer is achieved without reducing the number of spermatogonial stem cells in the testis and transgenic sperms and transgenic animals can easily be prepared.

15 Claims, 3 Drawing Sheets

METHOD OF GENE INTRODUCTION IN IN-VIVO SPERMATOGENIC CELL

TECHNICAL FIELD

The present invention relates to a method of producing a non-human vertebrate that harbours germ cells, particularly spermatogonial stem cells, having a desired gene transferred thereto, a non-human vertebrate that harbours germ cells having a desired gene transferred thereto, produced by the method, a method of producing transgenic sperms, transgenic sperms produced by the method, a method of producing a transgenic animal, a transgenic animal produced by the method of production and the like.

BACKGROUND ART

Germ cells have the unique ability to transmit parental genome information to the offspring. Germline modification has attracted significant attention in the last two decades because it provided a strategy to manipulate genes in vivo, and its application ranged from basic biomedical research to production agriculture (Manipulating the Mouse Embro, (Cold Spring Harbor Press, New York), pp 1-29, 2003). Current techniques to modify germline cells are based on oocytes, eggs or early embryos obtained from females. Developments in egg culture and transfer technology provided the groundwork for the modification of the germline cells obtained from females. However, although the technique is most widely used in mice, attempts to use germ cells obtained from females for other animal species has been limited due to their different reproductive behavior and difficulty in obtaining and manipulating eggs (Reproduction in farm animals, (Lippincott Silliams & Willins, Philadelphia, Pa.), pp 1-40, 2000), and it is difficult to obtain transgenic animals in more than 1% of injected embryos. Thus, there is clearly a need to establish new protocols for germline modification that have wider range of application.

While the female germ cells cease to proliferate before birth, all male germ cells originate from spermatogonial stem cells that have the ability to self-renew themselves (J. Androl., 21, 776-798, 2000). These cells continue to proliferate throughout life and support spermatogenesis. In contrast to differentiated germ cells that have limited life-span, stem cell-based transgenesis has a clear advantage in that transfected stem cells will continuously produce enormous number of transgenic sperm. A single rat stem cell with a transgene can continuously produce ~2000 transgenic spermatozoa (Histological and Histophathological Evaluation of the Testis, (Cache River Press, Clearwater, Fla.), pp. 1-40, 1990) and therefore numerous transgenic animals can be produced from a founder male. Towards this goal, several groups have succeeded in producing transgenic animals by transducing spermatogonial stem cells in vitro. Spermatogonial stem cells from mice and rats were infected with retrovirus during short-term culture and were transplanted into infertile recipient animals to produce spermatogenesis (Proc. Natl. Acad. Sci. USA, 98, 13090-13095, 2001; Proc. Natl. Acad. Sci. USA, 99, 14931-14936, 2002). By mating with females, recipients produced transgenic animals with efficiency comparable to female-based transgenic methods.

Although this technique provided a new possibility of male germline manipulation, it has several limitations. A major drawback of in vitro transduction approach is the low fertility rate of the recipient animals (Proc. Natl. Acad. Sci. USA, 91, 11298-11302, 1994). One of the reasons is that ablation of endogenous spermatogenesis, which is a prerequisite for efficient colonization of donor cells, often damages the environments of recipient testes for donor cell colonization (Tissue Cell, 31, 461-472, 1999; Biol. Reprod., 69, 412-420, 2003; Dev. Biol., 263, 253-263, 2003; Hum. Reprod., 18, 2660-2667, 2003). Furthermore, the absence of optimal culture condition for stem cells results in the significant decrease in stem cell number (Biol. Reprod., 67, 874-879, 2002; Biol. Reprod., 68, 2207-2214, 2003) and also contributes to lowered fertility. Only 10% of stem cells survive in vitro during 1 week ((Biol. Reprod., 67, 874-879, 2002; Biol. Reprod., 68, 2207-2214, 2003). Due to the rejection of allogeneic donor cells (Biol. Reprod., 68, 167-173, 2003; Reproduction, 126, 765-774, 2003; Biol. Reprod., 69, 1940-1944, 2003), the application of spermatogonial transplantation is still limited in most of other animal species in which immunocompatible recipients are not readily available. Because of these reasons, the efficiency of fertility restoration is limited after spermatogonial transplantation, and prevents the practical application of the technique for transgenesis.

A potentially competitive alternative to produce transgenic animals with spermatogonial stem cells is to introduce genes into stem cells in vivo, because it does not require transplantation or culture of stem cells. However, attempts of such direct transduction of spermatogonial stem cells have met with little success (Mol. Reprod. Dev, 233, 45-49, 1997; J. Virol., 63, 2134-2142, 1989; FEBS Lett., 475, 7-10, 2000; FEBS Lett., 487, 248-251, 2000; Hum. Gene Ther., 9, 1571-1585, 1998; Gene Dev., 1, 366-375, 1987; Biochem. Biophys. Res. Commun., 233, 45-49, 1997). In one study, transgene was integrated in the germline by in vivo electroporation, but the expression did not last long, and disappeared after long-term, indicating that the transgene was introduced into differentiated germ cells (Biol. Reprod., 59, 1439-1444, 1998). In another study, the transgene was not integrated into the germline and was found to be dominantly expressed in Sertoli cells (Biol. Reprod., 67, 712-717, 2002). The difficulty in transfecting spermatogonial stem cells in vivo cannot be explained only by the low number of stem cells in the testis (2 to 3 stem cells per 104 testis cells) (Cell and Molecular Biology of the Testis, (Oxford University Press, New York), pp 266-295, 1993; Mutation Res., 290, 193-200, 1993), since it was not possible with more efficient virus-based approach. Microinjection of various types of virus vectors into seminiferous tubules of adult testes also failed to transduce germline cells in vivo (Proc. Natl. Acad. Sci. USA, 99, 7524-7529, 2002; Proc. Natl. Acad. Sci. USA, 99, 1383-1388, 2002), and no animal studies have shown germline transmission by this approach. It is now considered that stem cells are protected in germline niche, which inhibits the access of the transgenes or virus particles to stem cells (FEBS Lett., 475, 7-10, 2000; Proc. Natl. Acad. Sci. USA, 99, 7524-7529, 2002).

In view of the above-described circumstances, the present invention is intended to provide a method of highly efficiently producing a non-human vertebrate that harbours germ cells having a desired gene transferred thereto by more efficiently transferring a desired gene to male germ cells, particularly spermatogonial stem cells.

DISCLOSURE OF THE INVENTION

The present inventors diligently investigated with the aim of accomplishing the above-described objects, found that by injecting a desired gene to the testis of a vertebrate wherein no tight junction exists between Sertoli cells, the desired gene can be very efficiently transferred to germ cells, and developed the present invention.

Accordingly, the present invention relates to the following:

(1) A method of producing a non-human vertebrate that harbours germ cells having a desired gene transferred thereto, comprising injecting the desired gene to the testis of a non-human vertebrate wherein no tight junction exists between Sertoli cells to transfer the desired gene to germ cells, so as to obtain a non-human vertebrate that harbours the germ cells.

(2) The method described in (1) above, wherein the germ cells are spermatogonial stem cells.

(3) The method described in (1) above, wherein the non-human vertebrate to receive an injection of the desired gene is infant.

(4) The method described in (1) above, wherein the desired gene is injected into the seminiferous tubule.

(5) The method described in (1) above, wherein the desired gene is incorporated in a vector.

(6) The method described in (5) above, wherein the vector is a viral vector.

(7) The method described in (6) above, wherein the viral vector is a retrovirus vector.

(8) The method described in (5) above, wherein the vector is a plasmid vector.

(9) The method described in (1) above, wherein the desired gene is transferred in a way such that it is incorporated in the chromosome of the germ cells.

(10) A non-human vertebrate that harbours germ cells having a desired gene transferred thereto, produced by the method described in (1) above.

(11) A method of producing transgenic sperms, comprising injecting a desired gene to the testis of a non-human vertebrate wherein no tight junction exists between Sertoli cells to transfer the desired gene to germ cells, so as to obtain sperms derived from the germ cells.

(12) Transgenic sperms produced by the method described in (11) above.

(13) A method of producing a non-human transgenic vertebrate, comprising injecting a desired gene to the testis of a non-human vertebrate wherein no tight junction exists between Sertoli cells to transfer the desired gene to germ cells, so as to obtain sperms derived from the germ cells, and fertilizing eggs by the sperms to obtain animal individuals having the desired gene transferred thereto.

(14) The method described in (13) above, wherein the eggs are fertilized by the sperms by natural mating.

(15) The method described in (13) above, wherein the eggs are fertilized by the sperms by microscopic insemination.

(16) The method described in (13) above, wherein the desired gene is transmitted to the offspring of the animal individuals.

(17) A non-human transgenic vertebrate produced by the method described in (13) above.

(18) A kit for producing a non-human vertebrate that harbours germ cells having a desired gene transferred thereto, comprising the following (i) and (ii):

(i) a non-human vertebrate wherein no tight junction exists between Sertoli cells;

(ii) a description bearing the statement that a non-human vertebrate that harbours germ cells having the desired gene transferred thereto can be produced, or should be produced, by injecting the desired gene to the testis of the vertebrate to transfer the desired gene to germ cells, so as to obtain a non-human vertebrate that harbours the germ cells.

(19) A kit for producing transgenic sperms, comprising the following (i) and (ii):

(i) a non-human vertebrate wherein no tight junction exists between Sertoli cells;

(ii) a description bearing the statement that transgenic sperms can be produced, or should be produced, by injecting a desired gene to the testis of the vertebrate to transfer the desired gene to germ cells, so as to obtain sperms derived from the germ cells.

(20) A kit for producing a non-human transgenic vertebrate, comprising the following (i) and (ii):

(i) a non-human vertebrate wherein no tight junction exists between Sertoli cells;

(ii) a description bearing the statement that a transgenic vertebrate can be produced, or should be produced, by injecting a desired gene to the testis of the vertebrate to transfer the desired gene to germ cells, so as to obtain sperms derived from the germ cells, and fertilizing the eggs by the sperms to obtain animal individuals having the desired gene transferred thereto.

Using the method of the present invention, even in animal species and lines for which in vitro transduction has been difficult, it is possible to obtain individuals harbouring germ cells, particularly spermatogonial stem cells, having a desired gene transferred thereto, at extremely high efficiency. Because gene transfer is achieved without reducing the number of spermatogonial stem cells in the testis, the fertility of the male to receive an injection of the gene is retained compared to in vitro transduction of germ cells, and transgenic sperms and transgenic animals can easily be prepared.

and (H), 100 μm in (B) to (E), and 20 μm in (F). Stain: X-Gal (A to H), hematoxylin and eosin(F).

Figure 3:
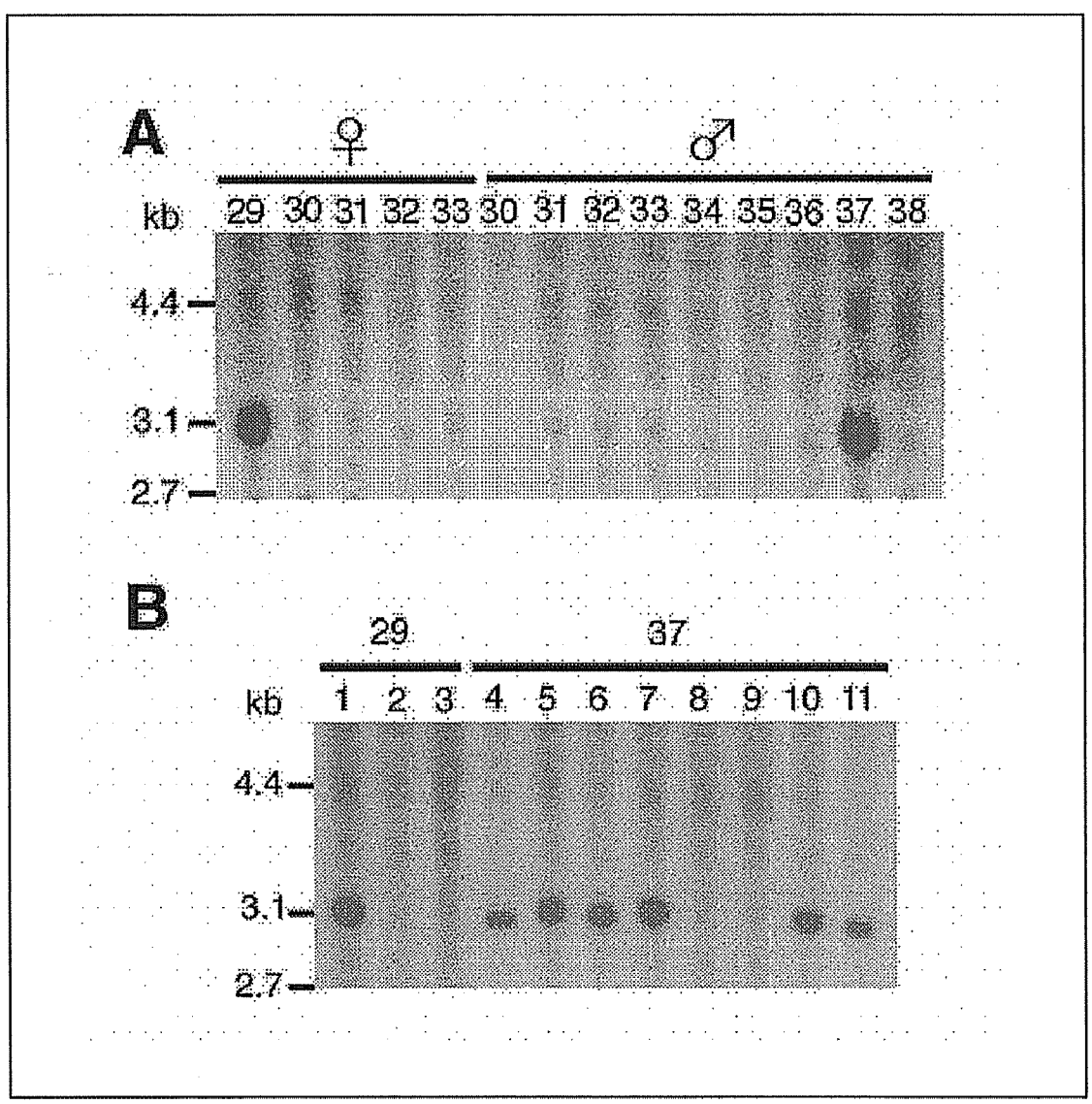

FIG. 3 shows Southern blot analysis of BamHI-digested tail genomic DNA from pups derived from #2B. (A) Result of an analysis of the DNA from F1 offspring derived from wild type females and #2B male mouse. Two (female #29 and male #37) of fourteen representative offspring contained the LacZ transgene. (B) Transmission of viral transgene to F2 generation. Both #58 (F1 female) and #70 (F1 male) transmitted the transgene to F2 generation.

DETAILED DESCRIPTION OF THE INVENTION

The method of the present invention of producing a non-human vertebrate that harbours germ cells having a desired gene transferred thereto comprises injecting the desired gene to the testis of a vertebrate wherein no tight junction exists between Sertoli cells to transfer the desired gene to germ cells, so as to obtain a non-human vertebrate that harbours the germ cells.

As examples of the vertebrate used in the present invention, a mammal, bird, fish, amphibian and reptile can be mentioned. Examples of the mammal include, but are not limited to, laboratory animals such as mice, rats, hamsters, guinea pigs and other rodents, and rabbits; domestic animals such as pigs, bovines, goat, horses, sheep, and minks; companion animals such as dogs and cats; and primates such as monkeys, rhesus monkeys, marmosets, orangutans, and chimpanzees. As the bird, chicken, partridges, ducks, geese, turkeys, ostriches, emus, ostriches, guinea fowls, pigeons and the like can be mentioned. The vertebrate is preferably a mammal.

The desired gene used in the method of the present invention is not subject to limitation, and may be an optionally chosen gene to be transferred. For example, a gene that encodes a polypeptide, a gene that encodes a functional nucleic acid molecule such as an antisense nucleic acid, siRNA, miRNA, stRNA, ribozyme, decoy nucleic acid, and the like can be mentioned. The gene is supplied as a nucleic acid (DNA or RNA).

The derivation of the desired gene is also not subject to limitation; the desired gene may be one derived from the same species of organism as the germ cells to have the desired gene transferred thereto, one derived from a different species of organism, one chemically synthesized, or a combination thereof. The size of the desired gene is also not subject to limitation, as long as the desired gene can be transferred to germ cells by the method of the present invention.

These desired genes may have an appropriate regulatory factor such as a promoter or enhancer for regulating the expression thereof added thereto.

The promoter is not subject to limitation, as long as it is capable of regulating the expression of the desired gene in germ cells, or in cells derived from an offspring animal derived from a germ cell having the desired gene transferred thereto. Using a tissue non-specific promoter, it is possible to regulate the expression of a desired gene in germ cells and in a broad range of tissues of an offspring animal derived from the germ cells. As examples of the tissue non-specific promoter, the CAG promoter, SRα promoter, EF1α promoter, CMV promoter, PGK promoter, U6 promoter, tRNA promoter and the like can be mentioned; according to the purpose, or according to the kind of desired gene to be expressed, a promoter can be chosen as appropriate. Using a tissue-specific promoter, it is possible to express the desired gene in a tissue specific manner in offspring animals derived from germ cells having the desired gene transferred thereto; for example, the desired gene can be expressed in a hapatocyte specific manner using the α1AT promoter, which is a liver-specific promoter, in a skeletal muscle specific manner using the skeletal muscle specific α-actin promoter, in a nerve specific manner using the nerve specific enolase promoter, and in a vascular endothelial cell specific manner using the vascular endothelial cell specific tie promoter.

A marker gene can be transferred together with a desired gene. Using a marker gene, it is possible to easily select germ cells having the desired gene transferred thereto. As the marker gene, fluorescent proteins such as green fluorescent protein, blue fluorescent protein, yellow fluorescent protein, cyan fluorescent protein, and red fluorescent protein, enzymes such as β-galactosidase and the like can be mentioned.

In the method of the present invention, the desired gene used for transfer may be incorporated in a vector. As the vector, plasmid vectors, PAC, BAC, YAC, viral vectors and the like can be mentioned, and the vector can be chosen as appropriate.

As the viral vector, retroviruses such as mouse Moloney leukemia retrovirus and lentivirus; adenovirus, herpesvirus, adeno-associated virus, parvovirus, Semliki Forest virus, vaccinia virus, Sendai virus and the like can be mentioned. Particularly, gene transfer using a retrovirus is preferable because the gene is transferred in a way such that it is incorporated in a chromosome. Lentivirus is capable of infecting both dividing and non-dividing cells and transferring a gene into both dividing and non-dividing cells.

A desired gene can be injected to the testis together with a gene transfer reagent. A gene transfer reagent refers to a reagent that promotes the transfer of a gene into cells by a mechanism involving the formation of a complex with the gene or with a vector incorporating the gene and the like.

When a viral vector, particularly a retrovirus vector, is used for gene transfer, retronectin, fibronectin, polybrene and the like can be used as gene transfer reagents.

When a plasmid vector and the like is used in gene transfer, lipofectin, lipfectamine, DIMRIEC, SuperFect and Effectin (Qiagen), unifectin, maxifectin, DOTMA, DOGS (Transfectam; dioctoadecylamideglycylspermine), DOPE (1,2-dioleoyl-sn-glycero-3-phosphoethanolamine), DOTAP (1,2-dioleoyl-3-trimethylammoniumpropane), DDAB (dimethyldioctoadecylammonium bromide), DHDEAB (N,N-di-n-hexaadecyl-N,N-dihydroxyethylammonium bromide), HDEAB (N-n-hexaadecyl-N,N-dihydroxyethylammonium bromide), polybrene, poly(ethyleneimine) (PEI) and the like can be used as gene transfer reagents.

In the present invention, a desired gene is injected to the testis of a vertebrate wherein no tight junction exists between Sertoli cells. In such a testis, the accessibility of the injected gene from the lumenal side of the seminiferous tubule to germ cells, particularly to spermatogonial stem cells, is high, so that the desired gene can be efficiently introduced to the cells. The vertebrate wherein no tight junction exists between Sertoli cells is not subject to limitation, as long as it is a male vertebrate having a tight junction between Sertoli cells that is morphologically or functionally incomplete compared to the tight junction between Sertoli cells of a healthy adult wild-type vertebrate of the same species. Those skilled in the art can easily determine whether or not a tight junction exists between Sertoli cells by histologically analyzing the testis isolated, and the like.

As examples of the vertebrate wherein no tight junction exists between Sertoli cells, infant animals (herein sometimes referred to as immature animals or pups), animals having the tight junction destroyed with a drug such as cadmium or cytokalacin, animals lacking the factor involved in the formation of tight junction between Sertoli cells and the like can be mentioned.

In the present invention, a infant animal refers to a postnatal animal younger than the time of formation of the tight junction between Sertoli cells in the growing process of the animal. Because the time of formation of the tight junction differs depending on the kind of vertebrate, it cannot be determined uniformly, but 2 weeks of age for mice, 2 to 3 weeks of age for rats, 10 weeks of age for rabbits, 20 to 32 weeks of age for cattle, 10 to 15 months of age for rhesus monkeys, 5 to 6 months of age for marmoset monkeys, and the like can be mentioned as examples.

Between Sertoli cells of a infant animal, there is no multilayer of differentiated germ cells as found in adult animals; this also improves the accessibility of a desired gene from the lumenal side of the seminiferous tubule to germ cells such as spermatogonial stem cells, and can contribute to an improvement in the efficiency of the transfer of the desired gene to germ cells. Furthermore, germ cells, particularly spermatogonial stem cells, of a infant animal, are more vigorously dividing than those of adult animals, are highly sensitive to gene transfer, and can contribute to an improvement in the efficiency of the transfer of the desired gene, and are particularly advantageous in gene transfer using a retrovirus vector.

In the method of the present invention, provided that a desired gene is injected to the testis so that it comes in contact with germ cells, the site of injection is not subject to limitation; in animals wherein no tight junction exists between Sertoli cells, because the accessibility from inside of the seminiferous tubule to germ cells is high, the desired gene is preferably injected into the seminiferous tubule.

In this case, the method of injecting the desired gene is not subject to limitation; for example, direct injection into the seminiferous tubule, injection from the efferent duct, injection from the rete testis and the like can be mentioned, and the method can be selected as appropriate in consideration of the kind of animal to receive the injection, ease of operation and the like. For example, in rodents such as mice, injection from the efferent duct is preferably used; in domestic animals such as cattle, injection from the rete testis is preferably used. When a desired gene is injected by the above-described method, the gene efficiently infiltrates the seminiferous tubule and reaches germ cell.

After injection of a desired gene to the testis, the desired gene can also be efficiently introduced to germ cells by applying an electric pulse to the testis (see, for example, JP-A-2001-309736).

In the method of the present invention, the germ cells to which a desired gene can be introduced are not subject to imitation, as long as they are male germ cells; for example, spermatogonial stem cells, spermatogonia, gonocytes, spermatogonia, primary spermatocytes, secondary spermatocytes, spermatids, sperms and the like can be mentioned. Particularly, because spermatogonial stem cells have the capability of self-renewal, continue to grow to support spermatogenesis throughout their life span, the cells having a desired gene transferred thereto are capable of constantly producing an enormous number of sperms having the desired gene transferred thereto; therefore, as the germ cells, spermatogonial stem cells are preferable.

By transferring a desired gene to germ cells by the above-described method to obtain sperms derived from the germ cells, transgenic sperms having the desired gene transferred thereto can be produced. The present invention provides a method of producing such transgenic sperms.

Whether or not the desired gene has been transferred to the germ cells can be determined by collecting germ cells or sperms from a vertebrate produced by the method of the present invention, and detecting the presence or absence of a region coming from the gene transferred to the cells. More specifically, the presence of the transgene can be detected by collecting chromosome DNA from the germ cells collected and the like, and performing amplification by a PCR method using a transgene specific primer pair, or a Southern blot method using a transgene specific probe and the like. Alternatively, whether or not the desired gene has been transferred to the germ cells can also be determined by detecting a product (protein and the like) of the desired gene.

Provided that a marker gene is transferred along with a desired gene, whether or not the desired gene has been transferred to germ cells can be determined by detecting the presence of the marker gene. For example, the presence or absence of transfer of the desired gene can be determined by detecting the fluorescence in the case of a fluorescent protein as the marker gene, or by using a chromogenic substrate corresponding to the enzyme in the case of an enzyme such as β galactosidase as the marker gene.

Alternatively, germ cells and sperms having a desired gene transferred thereto can be selected and isolated by a method known per se with a marker gene as an index.

If the gene transferred to germ cells is not incorporated in the chromosome, the gene undergoes degradation by the DNase present in cells and tissue and therefore disappears in a short time (about 2 weeks). If the transferred gene remains in the germ cells beyond this time, the gene is considered to be incorporated in the chromosome. According to the method of the present invention, a desired gene can be transferred to germ cells not only transiently, but also in a way such that it is incorporated in the chromosome. The gene incorporated in the chromosome of the germ cells can be stably transmitted even to the sperms and offsprings derived from the germ cells.

Because germ cells other than spermatogonial stem cells (i.e., differentiated germ cells) do not have the capability of self-renewal, the sperms produced from the cells are considered to disappear by the time taken for one cycle of spermatogenesis (about 35 days in mice) (see J. Androl., 21, 776-798, 2000, Cell and Molecular Biology of the Testis, (Oxford University Press, New York), pp. 266-295, 1993, Histological and Histopathological Evaluation of the Testis, (Cache River Press, Clearwater, Fla.), pp. 1-40, 1990). Therefore, the presence of the gene in germ cells, if observed even after elapse of the period after injecting the desired gene, demonstrates that the gene was transferred to spermatogonial stem cells. Because spermatogonial stem cells have the capability of self-renewal, continue to proliferate to support spermatogenesis throughout their life span, the cells having a desired gene transferred thereto are capable of constantly producing an enormous number of sperms having the desired gene transferred thereto. On the other hand, if a desired gene is transferred to germ cells other than spermatogonial stem cells, sperms having the gene transferred thereto will be transiently produced.

Furthermore, a transgenic animal can be produced by transferring a desired gene to germ cells by the above-described method to obtain sperms derived from the germ cells, and fertilizing eggs with the sperms to obtain an animal individual having the desired gene transferred thereto. The present invention provides such a method of producing a transgenic animal.

An egg refers to a female gamete that can be fertilized by a sperm. As examples of the egg, ovum, oocytes and the like can be mentioned.

Although fertilization of eggs with sperms can be performed by a commonly known method such as natural mating, microscopic insemination, or IVF, without limitation, it is preferable, in view of technical ease, that the fertilization be performed by natural mating. The natural mating is usually achieved by mating a male receiving an injection of a desired gene with a wild-type female.

When a marker gene is transferred to germ cells along with a desired gene and the like, an animal individual having the desired gene transferred thereto can be obtained at high efficiency by selecting and isolating sperms having the desired gene transferred thereto with the marker gene as an index, artificially inseminating eggs with the sperms (microscopic insemination, IVF and the like), and transplanting the eggs to the uterus of a pseudopregnant animal.

When an electric pulse is applied to the testis after injection of the desired gene to the testis, it is preferable to fertilize eggs with the sperms by microscopic insemination.

Whether or not the desired gene has been transferred to the animal individual obtained can be determined by collecting chromosome DNA from the animal individual obtained, and detecting the presence of the gene by amplification by a PCR method using a transgene specific primer pair, a Southern blot method using a transgene specific probe, and the like. Alternatively, whether or not the desired gene has been transferred to the animal individual can also be determined by detecting a product (protein) of the desired gene.

Furthermore, by mating the transgenic animal obtained with a wild-type animal of the same species, or with another transgenic animal of the same species, the transferred gene is further transmitted to the offspring thereof.

The present invention also provides a kit for producing a non-human vertebrate that harbours germ cells having a desired gene transferred thereto, comprising the following (i) and (ii):

(i) a non-human vertebrate wherein no tight junction exists between Sertoli cells;

(ii) a description bearing the statement that a non-human vertebrate that harbours germ cells having the desired gene transferred thereto can be produced, or should be produced, by injecting the desired gene to the testis of the vertebrate by the above-described method to transfer the desired gene to germ cells, so as to obtain a non-human vertebrate that harbours the germ cells. The kit may further comprise an optionally chosen gene, a control gene (a gene permitting easy confirmation of transfer thereof to germ cells; for example, a marker gene described above), a vector, a gene transfer reagent and the like. Using the kit, it is possible to easily produce a non-human vertebrate that harbours germ cells having an optionally chosen gene transferred thereto, by the above-described method.

The present invention also provides a kit for producing transgenic sperms, comprising the following (i) and (ii):

(i) a non-human vertebrate wherein no tight junction exists between Sertoli cells;

(ii) a description bearing the statement that transgenic sperms can be produced, or should be produced, by injecting a desired gene to the testis of the vertebrate by the above-described method to transfer the desired gene to germ cells, so as to obtain sperms derived from the germ cells. The kit may further comprise an optionally chosen gene, a control gene (a gene permitting easy confirmation of transfer thereof to germ cells; for example, a marker gene described above), a vector, a gene transfer reagent and the like. Using the kit, it is possible to easily produce transgenic sperms having an optionally chosen gene transferred thereto by the above-described method.

Furthermore, the present invention provides a kit for producing a non-human transgenic animal, comprising the following (i) and (ii):

(i) a non-human vertebrate wherein no tight junction exists between Sertoli cells;

(ii) a description bearing the statement that a transgenic animal can be produced, or should be produced, by injecting a desired gene to the testis of the vertebrate by the above-described method to transfer the desired gene to germ cells, so as to obtain sperms derived from the germ cells, and fertilizing eggs by the sperms to obtain an animal individual having the desired gene transferred thereto. The kit may further comprise a female animal for mating, an optionally chosen gene, a control gene (a gene permitting easy confirmation of transfer thereof to germ cells; for example, a marker gene described above), a vector, a gene transfer reagent and the like. Using the kit, it is possible to easily produce a transgenic animal having an optionally chosen gene transferred thereto by the above-described method.

Although the constituents of the above-described kit for producing a non-human vertebrate that harbours germ cells having a desired gene transferred thereto, kit for producing transgenic sperms, or kit for producing a transgenic animal may be provided in a single package as a whole, they may be provided separately in a plurality of packages.

The present invention is hereinafter described in more detail by means of the following Example, which, however, is not to be construed as limiting the scope of the invention.

EXAMPLE

Materials and Methods (Animals and Microinjection Procedure)

C57BL/6 (B6), BALB/C, C3H, DBA/2 and A mice were purchased from Japan SLC (Shizuoka, Japan). Both immature pups (5-10 days old) and adult (4-6 weeks old) mice were used for virus injection. In some experiments, operated mice were mated with wild-type B6 females to produce transgenic offspring. For the testicular injections, approximately 2 μl of DMEM/10% fetal calf serum (DMEM/FCS) containing retrovirus particles were introduced into the seminiferous tubules of an immature testis, while 10 μl were introduced into the tubules of a mature mouse testis, because the latter are larger. Microinjection was by efferent duct injection (Int. J. Dev. Biol. 41, 111-122, 1997), which filled 75-85% of the tubules in each recipient testis. Adult mice were anesthetized by Avertin injection (640 mg/kg). Pups were placed on ice to cause hypothermia-induced anesthesia (Proc. Natl. Acad. Sci. USA, 98, 6186-6191, 2001). In some experiments, only one testis was microinjected to avoid long-term exposure to ice. Pups were returned to their dams after the operation, and used for mating at least after 6 weeks.

(Preparation of Retrovirus)

A replication-defective ecotropic Moloney leukemia retrovirus, Gen-pgkbgal, was used to infect spermatogonial stem cells (J. Virol., 65, 2314-2319, 1991). This retrovirus expresses E. coli LacZ gene under the promoter of the phosphoglycerate kinase 1 (Pgk) gene, and was previously used to infect spermatogonial stem cells (Proc. Natl. Acad. Sci. USA, 98, 6186-6191, 2001 and FEBS Lett., 475, 7-10, 2000). Virus particle was stably produced from GP+E86 retrovirus packaging cells (J. Virol., 65, 2314-2319, 1991) in DMEM/FCS. The original virus titer was 3×105 colony-forming units/ml on NIH 3T3 cells. Virus-conditioned medium was collected from 24-hr cultures of confluent producing cells, passed through a 0.45-μm filter to remove contaminating cell debris and frozen at −80° C. till use. The procedure for virus concentration was previously described (Hum. Gene Ther., 7, 1735-1742, 1996). In brief, freeze-thawed virus stock was supplemented with 10 μg/ml of polybrene (Sigma), and 200 ml of viral supernatant was centrifuged for 16 hrs at 6000×g. The virus pellet was suspended in 1-2 ml of DMEM/FCS using 25G needle, and aliquotted in Eppendorf tubes. The virus supernatant was further centrifuged for additional 16 hrs at 6000×g, and suspended in 20-30 μl. The virus supernatant was used immediately after collection. The final titer of the retrovirus concentrate was ~109 colony-forming units/ml. All procedures for retrovirus preparation were performed at 4° C. The titer of the virus was significantly higher than those used in previous studies (Proc. Natl. Acad. Sci. USA, 98, 13090-13095, 2001, FEBS Lett., 475, 7-10, 2000), and can contribute to increasing gene transfer efficiency.

(Analysis of Testes)

To visualize infected cells, testes that received retrovirus injection were stained for LacZ expression with 5-bromo-4-chloro-3-indolyl β-D-galactoside (X-gal) (Wako Pure Chemical Industries, Osaka, Japan), as described (Biol. Reprod., 60, 1429-1436, 1999). A cluster of germ cells was defined as a colony when it occupied more than 50% of the basal surface of the tubule and was at least 0.1 mm long in length. The efficiency of colonization was evaluated by counting the total number of colonies under a stereomicroscope. All sections were stained with hematoxylin and eosin. Statistical analysis was performed by Student's t-test.

(Southern Blot)

Genomic DNA was isolated from tail samples from each offspring by phenol/chroloform extraction, followed by Ethanol precipitation. Ten μg of DNA was digested with BamHI, and separated on a 1.0% agarose gel. DNA transfer and hybridization was performed according to a conventional protocol. NcoI-BamHI fragment of LacZ cDNA (~1200 bp) was used as probe for hybridization.

Results (Infection of Spermatogonial Stem Cells by Retrovirus Injection into Seminiferous Tubules)

Figure 1:
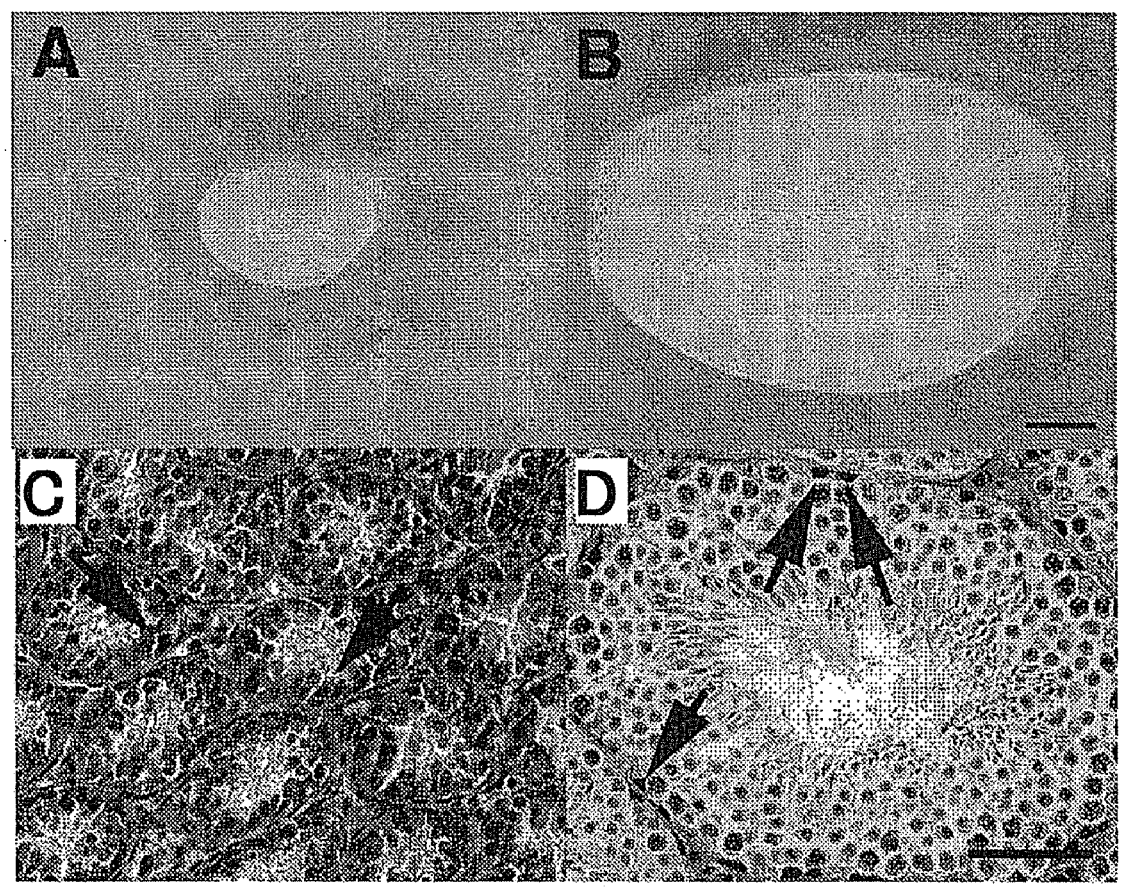
FIG. 1 shows Macroscopic and histological appearance of immature and mature testes. Pup (A and C) and adult (B and D) testes are shown. (A) Macroscopic appearance of a pup testis. (B) Macroscopic appearance of an adult testis. (C) Histological appearance of a pup testis. (D) Histological appearance of an adult testis. Arrows indicate spermatogonia. Note the absence of differentiated germ cells and different structure of the seminiferous tubules in the pup testis. Each bar corresponds to 1 mm in (A) and (B); and 50 µm in (C) and (D). Stain: hematoxylin and eosin stain.
Figure 2:
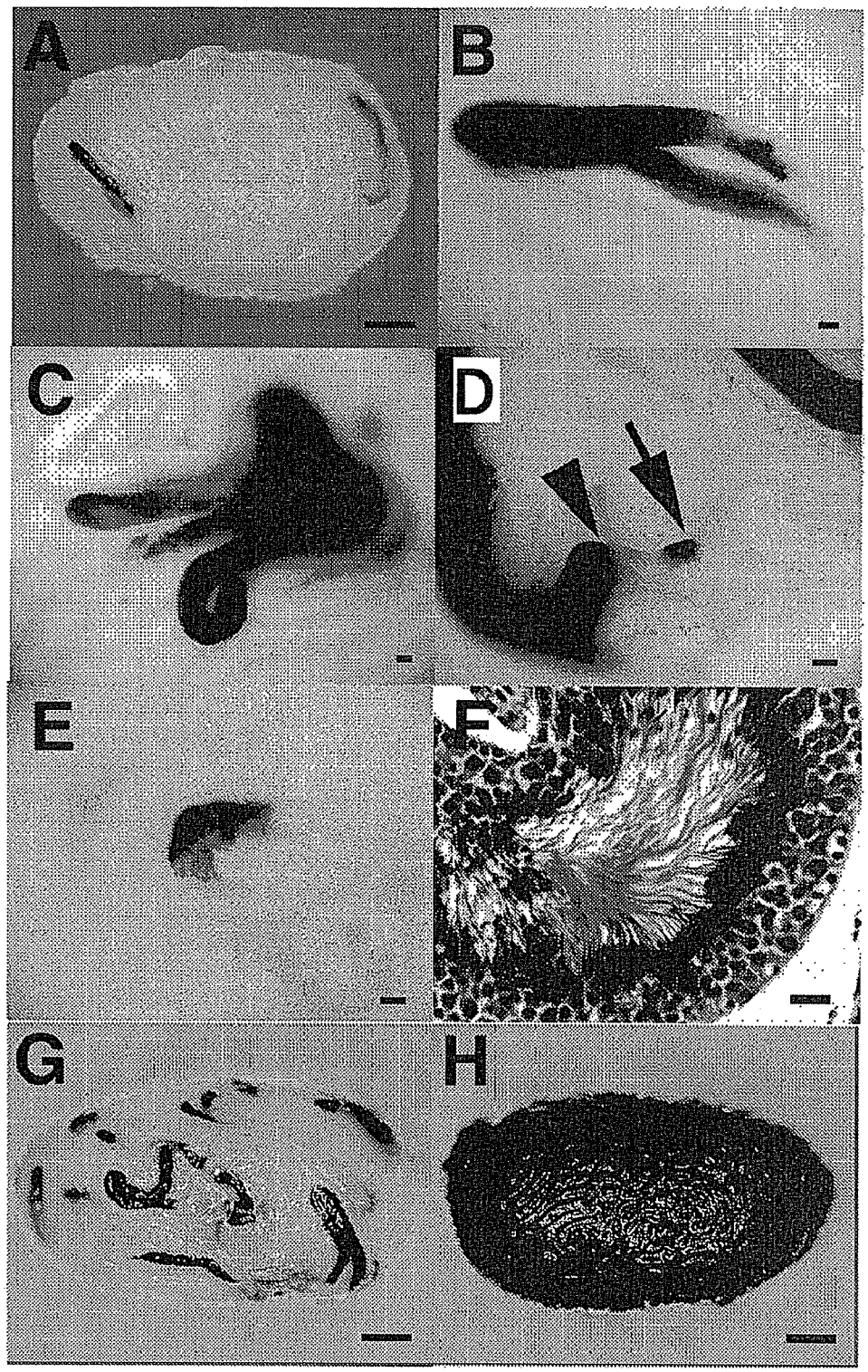
FIG. 2 shows retroviral transduction of spermatogonial stem cells. Blue tubules represent colonies from transduced spermatogonial stem cells. (A) Macroscopic appearance of a testis transduced by retrovirus. (B-E) Proliferation patterns of infected cells. (B) A typical colony in a transduced testis. The colony is asymmetric at the ends. (C) A similar asymmetric colony in the same testis. (D) A cluster of blue cells (arrow) in a different testis. Note the different staining pattern at the end of the colony (arrow head), as compared with those in (B) or (C). (E) A cluster of blue cells in a testis, which is similar to (D). (G) Histological appearance of section of seminiferous tubules from a transduced testis. Note the normal appearing spermatogenesis. Elongated spermatids are observed. (G) Macroscopic appearance of a testis from #2B. (H) Testes from a F1 offspring derived from mating #2B with wild-type female, indicating the germline transmission and expression of the transgene. Each bar corresponds to 1 mm in (A), (G)

Since there are multiple layers of germ cells and tight junction between Sertoli cells in the mature seminiferous tubules (Histological and Histopathological Evaluation of the Testis, (Cache River Press, Clearwater, Fla.), pp. 1-40, 1990). By contrast, immature testes had only one layer of spermatogonia and lack tight junction (FIG. 1). Based on these structural differences, the present inventor hypothesized that retrovirus microinjected into the immature seminiferous tubules would have better accessibility to spermatogonia, including stem cells than when injected to the mature seminiferous tubule. To test this possibility, concentrated Genpgkbgal retrovirus were microinjected into the seminiferous tubules of immature and mature testes of B6 mice, and compared for the infection efficiency. Two months after microinjection, the mice were sacrificed and their testes were stained for LacZ activity to examine for the presence of infected cells. While none of the 8 mature testes showed LacZ staining (data not shown), 3 of 6 immature testes showed cluster of LacZ positive cells (FIG. 2A), indicating retrovirus infection had successfully occurred. However, the pattern of LacZ staining was variable in these testes (FIG. 2B-E). Some of the LacZ-expressing clusters were long blue stretches of seminiferous tubules, resembling spermatogenic colonies from transplanted spermatogonial stem cells (Biol. Reprod., 66, 1491-1497, 2003). These colonies had asymmetric ends, and often had dark staining regions in center, which indicated that germ cell differentiation had occurred (FIGS. 2B and C). However, there were other clusters of LacZ-positive cells scattered widely in the seminiferous tubules (FIGS. 2D and E). Histological analysis revealed that spermatogenesis with LacZ staining, confirming that germ cells could be infected with this approach (FIG. 2F).

(Transgenic Mouse Production from Retrovirus-Infected Spermatogonial Stem Cells)

The present inventors next examined whether the infected retrovirus can produce transgenic animals. Retrovirus was microinjected into the seminiferous tubules of 5-10 day-old B6, C3H, BALB/C and A mice (founder mice). At least 2 separate experiments were performed for each strain. After 6 to 8 weeks, the animals were caged with two to three wild-type female mice to produce offspring. The results are shown in Tables 1 and 2.

TABLE 1

| Strain | Number of animals receiving injection* | Number of fertile animals (%) | Number of animals that caused females to bear transgenic offspring (%) |
| --- | --- | --- | --- |
| B6 | 17 | 12 (70) | 3 (18) |
| C3H | 4 | 4 (100) | 2 (50) |
| BALB | 9 | 9 (100) | 1 (11) |
| A | 6 | 6 (100) | 2 (33) |

Table 1 shows the efficiency of production of transgenic mice from different mouse strains.
*shows the results from 2 to 6 experiments.

TABLE 2

| Founder[a] | Strain | Time to analysis (number of days) | Testis weight (mg) R | Testis weight (mg) L | Colonies/ testis[b] R | Colonies/ testis[b] L | Time to birth of first transgenic animal[c] (number of days) | Transgenic animals/total progeny[d] (%) |
| --- | --- | --- | --- | --- | --- | --- | --- | --- |
| N | B6 | 479 | 87.5 | 86.0 | 2 | 0 | 82 | 4/132 (3.0) |
| 2A | B6 | 477 | 100.4 | — | 2 | — | 110 | 1/115 (0.9) |
| 2B | B6 | 477 | 110.7 | — | 21 | — | 174 | 4/123 (3.2) |
| 2N | C3H | 381 | 91.5 | — | 2 | — | 101 | 1/127 (0.8) |

TABLE 2-continued

| Founder[a] | Strain | Time to analysis (number of days) | Testis weight (mg) R | Testis weight (mg) L | Colonies/ testis[b] R | Colonies/ testis[b] L | Time to birth of first transgenic animal[c] (number of days) | Transgenic animals/total progeny[d] (%) |
|---|---|---|---|---|---|---|---|---|
| 2O | C3H | 273 | 85.2 | 80.2 | 1 | 3 | 177 | 1/59 (1.7) |
| 2Q | BALB | 314 | NA[a] | NA[a] | NA[a] | NA[a] | 50 | 6/150 (4) |
| 3I | A | 259 | — | 82.3 | — | 0 | 124 | 1/42 (2.4) |
| 3J | A | 260 | 96.6 | — | 0 | — | 97 | 4/61 (6.6) |

Table 2 shows the creation of transgenic mice from in vivo infected spermatogonial stem cells.
R, right testis; L, left testis. Two (1N and 2O) of the animals received virus injection on both sides.
NA[a], not applicable because the animal died before analysis (314 days after virus injection).
[b]Number of blue colonies in each testis; a cluster of germ cells was defined as a colony when occupying more than 50% of the basal surface of the tubule, and measuring at least 0.1 mm in length.
[c]Number of days from transplantation to birth of the first transgenic progeny sired by the animal.
[d]The numerator indicates the number of transgenic progeny; the denominator indicates the total number of progeny from each animal.

Although some of the injected animals could not sire offspring due to hernia associated with the operation (Proc. Natl. Acad. Sci. USA, 98, 6186-6191, 2001), an average of 86% of animals that received retrovirus started to sire offspring (Table 1). The weight of the testis was comparable to that of the normal, untreated mice. All offspring resulted from the mating with wild-type females were examined for the presence of transgene by Southern blotting using LacZ gene specific probe, and 40 to 132 offspring from each founder mouse were examined during 6 to 16 months after the operation.

In total, 26% (8/31) of fertile animals sired offspring with the transgene during the analysis period (Table 1). The percentage of transgenic animals produced from the founder males ranged from 0.8 (1/127) to 6.6% (4/61), with an average of 2.8% (Table 2). Because only half of the parental chromosome will be transmitted from the spermatogonial stem cells to the offspring, the result indicates that 5.6% of spermatozoa derived from the transduced stem cells. Although the numbers of animals may be too few to conclude a genetic effect of strains used to transduce stem cells, 2 of 4 (50%) C3H mice produced transgenic progeny (Table 1). In contrast, 1 of 9 (11%) BALB/C mice produced progeny with the LacZ transgene. The first transgenic appeared in the progeny from a BALB/C founder mouse as early as 50 days after retrovirus injection, with an average of 114 days. The transgene was originated from spermatogonial stem cells that had been infected with the retrovirus, since spermatozoa generated from differentiated germ cells will disappear by 35 days (J. Androl., 21, 776-798, 2000, Cell and Molecular Biology of the Testis, (Oxford University Press, New York), pp. 266-295, 1993, Histological and Histopathological Evaluation of the Testis, (Cache River Press, Clearwater, Fla.), pp. 1-40, 1990).

The founder animals were next sacrificed after 259 to 479 days to examine the degree of retrovirus infection. LacZ staining in the testis was found regardless of whether the animals produced transgenic offspring (FIG. 2G). However, the number of blue colonies was significantly greater for founder animals that produced transgenic offspring than those with non-transgenic progeny (3.44±2.22 vs 0.03±0.03 colonies/testis; mean±standard error; P<0.05). On the other hand, no significant relationship was found between the number of colonies and the percentage of transgenic progeny from a founder mouse. Interestingly, in two (#3I and 3J) of the recipients that produced transgenic offspring, no blue colonies were found at the time of examination, suggesting that stem cells with the transgene might have finished their growth or have disappeared. However, histological analysis of the testes from other founder mice showed complete spermatogenesis with normal appearing organization (data not shown). Expression of LacZ transgene in hemizygous F1 mice was observed in several organs in different animals (FIG. 2H).

Finally, we examined whether the transgene can be transmitted to the next generation. We used both male and female offspring from #2B founder mice, and each transgenic mouse was mated with non-transgenic wild-type B6 mouse to generate F2 offspring. Six of eight offspring from the male transgenic mouse and one of three offspring from the female mouse showed the presence of transgene by Southern blot analysis (FIG. 3), confirming the stable transmission of the transgene. The expression of LacZ transgene in F2 animals was similar to that of F1 generation.

Discussion

According to the method of the present invention, transduction to germ cells such as spermatogonial stem cells can be achieved in vivo to produce transgenic animals.

An advantage of the method of the present invention over conventional in vitro transfection resides in that because gene transfer is achieved without reducing the number of spermatogonial stem cells in the testis, the fertility of the male receiving an injection of the gene is retained.

In this study, we demonstrated that spermatogonial stem cells can be transduced in vivo and produce transgenic animals. One of the important advantages of the technique is that the technique does not depend on genetic background of the animals. In spermatogonial transplantation, extensive colonization of donor cells is a prerequisite for fertility restoration. It is estimated that at least 15% of stem cells are required to restore fertility after ablation treatment. However, this is difficult to achieve, because the number of stem cells decreases even during short-time culture and only a limited amount of cells can be reintroduced into seminiferous tubules. Moreover, the ablation of endogenous germ cells for transplantation not only damages the germ cell environment for fertility restoration, but also exerts systemic toxicity. Indeed, the ablation protocol is difficult to optimize due to strain or age differences in the sensitivity to ablation. In contrast, the current approach employs the intact, wild-type animals. Because their testes have normal number of stem cells, they could sire offspring efficiently after virus injection.

Another important advantage of the method of the present invention is that the method does not depend on genetic background of the animals. While the success of in vitro transduction approach is influenced by the genetic background due to problems associated with spermatogonial transplantation. In fact, transgenic offspring from mouse spermatogonial stem cell have been obtained only from genetically infertile mutant recipients due to difficulty in host preparation and donor cell rejection (Proc. Natl. Acad. Sci. USA, 98, 13090-13095, 2001). In contrast, the transgenic offsprings were able to be produced in four different strains using the method of the present invention, suggesting the promising direction to solve this problem. Although the percentage of animals that produced transgenic offspring was lower than those using in vitro approach (22% in the above-described Example vs. 33-38% in previous studies), this could be potentially improved by using higher titer preparations and by using a particular type of retrovirus, such as lentivirus. Thus, the method of the present invention will overcome the difficulties associated with the in vitro gene transfer approach and increase the opportunity to manipulate germ cells such as spermatogonial stem cells.

An interesting observation from the above-mentioned Example is the variable patterns of LacZ staining in the retrovirus-infected testes. While colonies developed in stem cell-depleted testis are generally uniform and have symmetric ends (Biol. Reprod., 60, 1429-1436, 1999), those observed in the above-mentioned Example were of variable patterns and had asymmetric ends. Since the LacZ staining likely originated from transduction of single stem cells, the results form the above-mentioned Example suggest that spermatogonial stem cells in wild-type testes proliferate in a different manner from the donor stem cells in ablated environment, and that the behavior of spermatogonia or spermatogonial stem cells may be quite variable in the normal course of spermatogenesis. This is in agreement with a recent report that pattern of spermatogenesis from transplanted stem cells is influenced by the presence of other germ cells in the seminiferous tubules (Biol. Reprod., 66, 1491-1497, 2003). In fact, the colony patterns in the above-mentioned Example showed remarkable resemblance to donor cell-derived colonies observed in wild-type recipient testis after spermatogonial transplantation. Such interaction between germ cells was previously shown in several other studies (Biol. Reprod., 66, 1491-1497, 2003, Cell Tissue Kinet., 7, 165-172, 1974, Arch. B cell Pathol. Include. Mol. Pathol., 33, 67-80, 1980), and considered to be mediated by "chalone", tissue-specific inhibitor of stem cell proliferation. Although proliferation kinetics of stem cells is well studied in other self-renewing tissues by specifically marking individual stem cells by retrovirus (Genes Dev., 4, 220-232, 1990, J. Invest. Dermatol., 109, 377-383, 1997), very little is known about the dynamics of spermatogonial stem cell proliferation and its regulation. Further studies using in vivo stem cell transduction by the method of the present invention will be useful for such analysis.

A potentially important application of the method of the present invention is the transgenesis of animals, for which conventional transgenic technology is impossible or inefficient (Reproduction in farm animals, (Lippincott Silliams & Willins, Philadelphia, Pa.), pp. 1-40, 2000). While recent establishment of long-term culture system for spermatogonial stem cells in mice and bulls may improve in vitro transduction method and potentially lead to new developments in animal transgenesis (Biol. Reprod., 68, 272-281, 2003, Biol. Reprod., 69, 612-616, 2003, J. Androl., 24, 661-669, 2003), such culture system possibly necessitate further improvements in culturing conditions for many other species, and the problems associated with spermatogonial transplantation need to be resolved. In particular, ablation of endogenous germ cells is even more difficult or toxic in large animal species due to their large body size, different testicular structure and endocrinological environment. Moreover, although several procedures to enrich stem cells is established in rodents and could be used to enhance fertility restoration rate (Proc. Natl. Acad. Sci. USA, 97, 8346-8351, 2000, EMBO Rep. 3, 753-759, 2002, Biol. Reprod., 70, 70-75, 2004), spermatogonial stem cells in other animals are less characterized, and methods to enrich stem cells has not been available. However, since the microinjection technique is already established for many animal species (Hum. Reprod., 17, 55-62, 2002, Hum. Reprod., 14, 144-150, 1999), microinjection of virus vectors into immature animals can be readily extended to other animal species. Immature testes in domestic animals generally exert less resistance against the flow of injection into seminiferous tubules, and facilitate the application of the present technique (Hum. Reprod., 14, 144-150, 1999). Thus, in vivo transduction of spermatogonial stem cells now provides a novel strategy for manipulating spermatogonial stem cells, and accelerates efforts to understand and use this valuable population of cells.

INDUSTRIAL APPLICABILITY

Using the method of the present invention, even in animal species and lines for which in vitro transduction has been difficult to date, it is possible to obtain individuals harbouring germ cells, particularly spermatogonial stem cells, having a desired gene transferred thereto, at extremely high efficiency. Also, the fertility of the male to receive an injection of the gene is retained, compared to in vitro transduction of germ cells, because gene transfer is achieved without reducing the number of spermatogonial stem cells in the testis, and transgenic sperms and transgenic animals can easily be prepared. Therefore, using the method of the present invention, by introducing an optionally chosen gene to a domestic animal, breeding of the domestic animal is possible, and the method is useful in the field of agriculture. Also, using the method of the present invention, it is possible to cause animals to produce various useful substances, and the method is useful in the field of pharmaceuticals and medical care.

This application is based on a patent application No. 2004-158174 filed on May 27, 2004 in Japan, the contents of which are incorporated in full herein by this reference.

The invention claimed is:

1. A method of producing a non-human vertebrate that harbours spermatogonial stem cells having a desired gene transferred thereto, comprising injecting a vector comprising (a) the desired gene and (b) a promoter capable of regulating the expression of the desired gene into the testis of a non-human vertebrate wherein no tight junctions exist between Sertoli cells, such that spermatogonial stem cells of the testis are transfected with the vector, so as to obtain a non-human vertebrate that harbours the spermatogonial stem cells comprising the desired gene.

2. The method of claim 1, wherein the non-human vertebrate is immature.

3. The method of claim 1, wherein the vector is injected into the seminiferous tubule.

4. The method of claim 1, wherein the vector is a viral vector.

5. The method of claim 4, wherein the viral vector is a retrovirus vector.

6. The method of claim 1, wherein the vector is a plasmid vector.

7. The method of claim 1, wherein the desired gene is incorporated in a chromosome of the spermatogonial stem cells.

8. A method of producing transgenic sperm comprising injecting a vector comprising (a) a desired gene and (b) a promoter capable of regulating the expression of the desired gene into the testis of a non-human vertebrate, wherein no tight junctions exist between Sertoli cells, such that spermatogonial stem cells of the testis are transfected with the vector, and then obtaining transgenic sperm from the non-human vertebrate.

9. A method of producing a non-human transgenic vertebrate, comprising injecting a vector comprising (a) a desired gene and (b) a promoter capable of regulating the expression of the desired gene into the testis of a non-human vertebrate, wherein no tight junctions exist between Sertoli cells, such that spermatogonial stem cells of the testis are transfected with the vector, and then fertilizing eggs by transgenic sperm from said non-human vertebrate to obtain a non-human transgenic vertebrate having the desired gene.

10. The method of claim 9, wherein the eggs are fertilized by the sperm by natural mating.

11. The method of claim 9, wherein the eggs are fertilized by the sperm by microscopic insemination.

12. The method of claim 9, wherein the desired gene is transmitted to the offspring of the non-human transgenic vertebrate.

13. The method of claim 1, wherein the non-human vertebrate is a postnatal mouse younger than 2 weeks of age.

14. The method of claim 13, wherein the mouse is 10 days of age or younger.

15. A method of producing a mouse that harbours spermatogonial stem cells having a desired gene transferred thereto, comprising injecting a viral vector comprising (a) the desired gene and (b) a promoter capable of regulating the expression of the desired gene in the testis of a mouse which is 10 days of age or younger wherein no tight junctions exist between Sertoli cells, such that spermatogonial stem cells of the testis are transfected with the vector, so as to obtain a mouse that harbours the spermatogonial stem cells comprising the desired gene.

* * * * *